United States Patent [19]

Hirsch et al.

[11] 4,403,099
[45] Sep. 6, 1983

[54] SILICON-CONTAINING NITRO DYES AND PROCESS FOR MAKING THE SAME

[75] Inventors: Bodo Hirsch, Graupa; Gunter Horn, Nuenchritz; Hellmut Reuther, Dresden, all of German Democratic Rep.

[73] Assignee: VEB Chemiewerk Nünchritz, Radebeul, German Democratic Rep.

[21] Appl. No.: 352,830

[22] Filed: Feb. 26, 1982

Related U.S. Application Data

[63] Continuation of Ser. No. 27,265, Apr. 5, 1979, abandoned.

[30] Foreign Application Priority Data

Apr. 5, 1978 [DD] German Democratic Rep. ... 204587

[51] Int. Cl.³ .................................................. C07F 7/10
[52] U.S. Cl. .................................................. 556/422
[58] Field of Search ...................................... 556/422

[56] References Cited

U.S. PATENT DOCUMENTS

| | | | |
|---|---|---|---|
| 2,256,246 | 7/1956 | Burkhard | 556/422 |
| 2,985,680 | 5/1961 | Pepe | 556/422 X |
| 2,998,406 | 8/1961 | Bailey et al. | 556/422 X |
| 3,131,205 | 4/1964 | Frankel | 556/422 |
| 4,139,403 | 2/1979 | Baum et al. | 556/422 X |

*Primary Examiner*—Paul F. Shaver
*Attorney, Agent, or Firm*—Gabriel P. Katona

[57] ABSTRACT

Disclosed are silicon-containing nitro dyes of the formula:

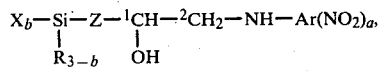

wherein the coloring component is bonded with a Si-atom by homopolar bonds and wherein X represents same or different hydrolyzable groups or a silicone radical;

Z is a bivalent alkylene radical with 2 to 10 C-atoms, which may be interrupted by oxygen and may also contain cyclic radicals, and wherein $^1C$ and $^2C$ may be parts of a cycloalkyl ring;

R is a monovalent organic radical;

Ar is a substituted or unsubstituted aryl radical;

a and b are integers from 1–3;

and a process for making said dyes. Said dyes may be built into the polymer molecules or affixed to fibers without additional fixation.

5 Claims, No Drawings

SILICON-CONTAINING NITRO DYES AND PROCESS FOR MAKING THE SAME

CROSS-REFERENCE TO RELATED APPLICATION

This application is a continuation of application Ser. No. 027,265, filed Apr. 5, 1979, now abandoned.

SUMMARY OF THE INVENTION

The present invention relates to silicon-containing nitro dyes for dyeing a variety of organic and inorganic materials, e.g. organic polymers or organosiloxanes and especially for coloring silicone products. The dyes may be built into the polymer molecules or applied to fibers without additional fixation, respectively.

BACKGROUND AND PRIOR ART

BONJOUR (Dissertation, 1970, ETH Zuerich) and HASHIMOTO (Yakugaki Zasshi 80, (1960), 1399–1404) describe the preparation of azo dyes on the basis of trimethylsilanilines by reaction of these silicon compounds with diazotized aromatic amines. Dyes of this type are not suitable for adhering to the substances to be dyed because of their inactive methyl groups at the silicon atom. They have consequently not resulted in industrial use of any importance.

From U.S. Pat. Nos. 3,888,891, 3,963,774 and 3,981,859 dyes have become known which contain a tris-(trimethylsiloxy-)silylalkylamino radical. These are mainly quinone-, indigo-, thioindigo-, phthalocyanine- and azo dyes. Apart from the fact that for the preparation of the tris-(trimethylsiloxy-)silylalkylamino compound expensive reactions have to be carried out and the silane is only obtained in a low yield, these dyes have only limited use in the dyeing of certain polyorganosiloxanes because their siloxy radicals are very ineffective.

Silicon-containing dyes, which already have a hydrolyzable radical capable of imparting adherence, are for instance described in U.S. Pat. Nos. 2,925,313, 2,927,839, 2,931,693, 2,934,459, 2,955,898, 2,955,899 and 2,963,338. In these cases, arylamino- or aminoarylalkylalkoxy-silanes were used as starting compounds for the production of azo dyes. These dyes adhere well to glass fibers, natural fibers, such as wool, silk and cotton, as well as to synthetic fibers. A disadvantage, however, In that case, too, the preparation of the silicon-containing amino starting materials is cumbersome and expensive, and the results are unsatisfactory.

Silicon-containing nitro dyes of the structure disclosed by the invention have not been described in the literature up to now.

OBJECT OF THE INVENTION

It is the object of the present invention to produce so far unknown dyes from easily available starting materials in a simple and inexpensive manner, and in good yields. The chromophone components are to be bonded to the polymer structures, if possible, by homopolar bonds.

Furthermore, the stability and lasting coloring property of the novel dyes should come up to the high and particular specifications of silicone technology and they should be capable of dyeing polymer materials, especially silicone products, for lasting effects.

DETAILED DESCRIPTION OF THE INVENTION

It has been found that silicon-containing nitro dyes according to the invention will fulfill the objects above indicated. The dyes have the general formula

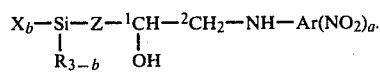

Of the high qualifications mentioned above, expected from the products according to the invention, we may mention, by way of example, temperature stability.

In the general formula:

X represents equal or different hydrolyzable groups or a siloxane radical

Z is a bivalent alkylene radical with 2 to 10 C-atoms which may interrupted by oxygen and may also contain cyclic radicals, and wherein $^1C$ and $^2C$ may be parts of a cycloalkyl ring R is a monovalent organic radical Ar is a substituted or unsubstituted aryl radical a and b are integers from 1 to 3

The production of the novel silicon-containing nitro dyes according to the invention is very simple and can be brought about by reacting silanes or siloxanes of the general formula

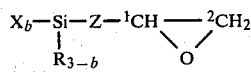

with nitroanilines of the general formula

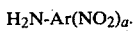

In the formulas, the symbols X, Z, R, Ar, a and b have the same meanings as explained before.

For the reaction, the epoxy-functional silanes or siloxanes are mixed with the nitroanilines and heated to boiling temperature. The starting materials are so chosen that in the reaction mixture stoichiometric amounts of the epoxy- and amino groups will be present. The reaction takes place quantitatively and without difficulties. If the nitroaniline is difficultly soluble in the silane or siloxane, the reaction can be carried out in a solvent.

Suitable solvents are methanol, ethanol, acetone, dimethylformamide, carboxylic alkyl esters, benzene and toluene. There is no need to add a catalyst. Since in the performance of the reactions according to the invention the functional groups at the Si-atom are maintained intact, it is possible to use partial silicon condensates as starting materials, which lead to products useful as toning pastes.

The nitro dyes according to the invention, wherein the dye is built into the silicon molecule by means of a homeopolar bond, are further useful for coloring of polysiloxanes and organic polymers, of siliconic fillers, where the hydrolyzable groups at the silicon atom form homopolar bonds with the materials to be dyed, which are a prerequisite for the high quality, e.g. light and migration stabilities.

The nitro dyes according to the invention are furthermore suited as reactive dyes suitable for coloring natural and synthetic fibers, such as wool, silk, cotton, regenerated fibers, polyamides, polyesters and so on, because the reactive groups present in the dyestuff molecule form homopolar bonds with the substrate.

EXAMPLES

The invention will now be more fully described in a number of examples which are given by way of illustration and not of limitation; all parts given are by way of mass.

EXAMPLE 1

27.6 parts of 4-nitroaniline are dissolved with 300 parts of ethanol at elevated temperature and mixed with 51.8 parts 3-glycidoxypropyl-trimethoxysilane. The mixture is refluxed for 4 hours and then the solvent is distilled off. Obtained is a yellow-red dye.

One g of the so obtained dye is stirred with 50 g of a paste consisting of 100 parts of α-ω-polydimethylsiloxanediol and 50 parts of an amorphous silicondioxide. After thorough mixing of the paste with 2 g of a cross-linking liquid containing 80 parts of tetraethoxysilane and 20 parts of dibutyltindilaurate, the mass is allowed to stand for 48 hours at room temperature, whereupon a yellow-colored silicon rubber is obtained, which does not loose its color even after being heated to 180° C. for 10 hours.

EXAMPLE 2

36.6 parts of 2,4-dinitroaniline are added in batches to 56.0 parts of 3-glycidoxypropyl-triethoxysilane heated to 150° C. After the addition is completed, the reaction mixture is maintained for 5 hours at a temperature of 200° C. After cooling, a brown dye is obtained.

A 5% dye solution is prepared with ethanol, into which cotton, wool, silk, polyamide-, polyester- and glass fibers are dipped for 5 minutes each. The dyed fibers are subsequently washed with water and ethanol. In this manner, yellow-colored fibers are obtained which are distinguished by high fastness to light.

EXAMPLE 3

24.6 parts of β-3,4-epoxycylohexylethyltrimethoxysilane are mixed with 18.4 parts of 2,4-dinitroaniline and heated to 180° C. for two hours. 4.8 g unreacted β-3,4-epoxycyclohexylethyltrimethoxysilane can be distilled off by vacuum distillation. The residue is washed with ethanol and filtered. Obtained is a brown-yellow powder.

One g of this nitro dye is mixed with 100 g of a 70% toluene solution of a spatially cross-linked methylphenylsilicone resin. Subsequently, the silicone-resin solution is predried in a mold at 80° C., and thereafter hardened to completion for about 3 hours at 250° C. Obtained is a transparent yellow silicone-resin body.

We claim:

1. Silicon-containing nitro dyes having the following formula:

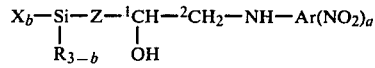

wherein the coloring component is bonded with a Si-atom by homopolar bonds and wherein X represents same or different hydrolyzable groups or a silicone radical;

Z is a bivalent alkylene radical with 2 to 10 C-atoms, which may be interrupted by oxygen and may also contain cyclic radicals, and wherein $^1C$ and $^2C$ may be parts of a cycloalkyl ring;

R is a monovalent organic radical;

Ar is a substituted or unsubstituted aryl radical;

a and b are integers from 1-3.

2. Process for making silicon-containing nitrodyes having the formula:

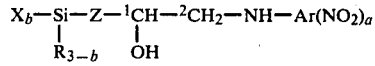

comprising the step of, reacting silanes or siloxanes of the formula:

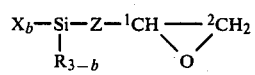

with nitroanilines of the formula:

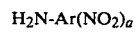

wherein

X represents same or different hydrolyzable groups or a siloxane radical;

Z is a bivalent alkylene radical with 2-10 C-atoms which may be interrupted by oxygen and may also contain cyclic radicals, and wherein $^1C$ and $^2C$ may be parts of a cycloalkyl ring;

R is a monocalent organic radical;

Ar is a substituted or unsubstituted aryl radical, and a and b are integers from 1 to 3; the reaction being carried out at temperatures from 100° C. to 200 C. in stoichiometric ratio with respect to the epoxy group of the first reactant and the amino group of nitroaniline.

3. Process of claim 2 wherein the reaction is carried out in a solvent.

4. Process of claim 2 wherein the silanes or siloxanes contain glycidoxy groups.

5. Process of claim 2 wherein the starting silanes or siloxanes contain alicyclic groups of epoxy structure.

* * * * *